(12) United States Patent
Cowe

(10) Patent No.: US 10,159,807 B2
(45) Date of Patent: Dec. 25, 2018

(54) PEN INJECTOR APPARATUS

(71) Applicant: OWEN MUMFORD LIMITED, Oxfordshire (GB)

(72) Inventor: Toby Cowe, Oxfordshire (GB)

(73) Assignee: OWEN MUMFORD LIMITED, Oxfordshire (GB)

( * ) Notice: Subject to any disclaimer, the term of this patent is extended or adjusted under 35 U.S.C. 154(b) by 358 days.

(21) Appl. No.: 14/433,156

(22) PCT Filed: Oct. 4, 2013

(86) PCT No.: PCT/GB2013/052587
§ 371 (c)(1),
(2) Date: Apr. 2, 2015

(87) PCT Pub. No.: WO2014/053848
PCT Pub. Date: Apr. 10, 2014

(65) Prior Publication Data
US 2015/0265775 A1    Sep. 24, 2015

Related U.S. Application Data

(60) Provisional application No. 61/709,459, filed on Oct. 4, 2012.

(30) Foreign Application Priority Data

Oct. 4, 2012  (GB) .................................. 1217765.5

(51) Int. Cl.
*A61M 5/315*   (2006.01)
*A61M 5/32*    (2006.01)
(Continued)

(52) U.S. Cl.
CPC .......... *A61M 5/329* (2013.01); *A61M 5/1424* (2013.01); *A61M 5/16809* (2013.01);
(Continued)

(58) Field of Classification Search
CPC .............. A61M 5/16809; A61M 39/22; A61M 2039/226; A61M 2039/2486;
(Continued)

(56) References Cited

U.S. PATENT DOCUMENTS

| 5,988,452 | A | 11/1999 | Dent et al. |
| 2012/0004641 | A1* | 1/2012 | Bruehwiler ....... A61M 5/31553 604/506 |

FOREIGN PATENT DOCUMENTS

| EP | 2335757 A2 | 6/2011 |
| FR | 2167036 A5 | 8/1973 |

(Continued)

OTHER PUBLICATIONS

International Search Report, dated Feb. 7, 2014, from corresponding PCT application.

(Continued)

*Primary Examiner* — Deanna K Hall
(74) *Attorney, Agent, or Firm* — Young & Thompson

(57) ABSTRACT

A pen injector apparatus is disclosed for use with a cartridge to deliver a plurality of single metered doses therefrom. The injector apparatus includes a body arranged to provide a conduit which, in use, provides a fluid communication path between the cartridge and a delivery needle and a mechanism arranged to expel therapeutic material from the cartridge. The mechanism is arranged to draw therapeutic material from the cartridge into the conduit by negative pressure and discharge a metered dose from the conduit via the delivery needle.

14 Claims, 3 Drawing Sheets

(51) Int. Cl.
    *A61M 5/168*     (2006.01)
    *A61M 5/20*     (2006.01)
    *A61M 5/24*     (2006.01)
    *A61M 5/31*     (2006.01)
    *A61M 5/34*     (2006.01)
    *A61M 5/142*     (2006.01)
    *A61M 5/00*     (2006.01)

(52) U.S. Cl.
    CPC .............. *A61M 5/204* (2013.01); *A61M 5/24* (2013.01); *A61M 5/2429* (2013.01); *A61M 5/3146* (2013.01); *A61M 5/3156* (2013.01); *A61M 5/3159* (2013.01); *A61M 5/31548* (2013.01); *A61M 5/31553* (2013.01); *A61M 5/31593* (2013.01); *A61M 5/3202* (2013.01); *A61M 5/344* (2013.01); *A61M 5/002* (2013.01)

(58) Field of Classification Search
    CPC ...... A61M 5/145; A61M 5/2053; A61M 5/20; A61M 5/315; A61M 5/14526; A61M 5/142; A61M 5/1452
    See application file for complete search history.

(56) References Cited

FOREIGN PATENT DOCUMENTS

| WO | 0100261 A1 | 1/2001 | | |
|---|---|---|---|---|
| WO | WO2010077278 A1 | 7/2010 | | |
| WO | 2010091132 A | 8/2010 | | |
| WO | 2010118764 A1 | 10/2010 | | |
| WO | WO 2010118764 A1 * | 10/2010 | ........... | A45D 34/042 |
| WO | 2011092536 A1 | 8/2011 | | |

OTHER PUBLICATIONS

Great Britainl Search Report, dated Jan. 7, 2013, from corresponding PCT application.

* cited by examiner

PEN INJECTOR APPARATUS

FIELD OF THE INVENTION

This invention relates to a pen injector apparatus and in particular, but not exclusively, to such apparatus used for injecting metered doses from a cartridge of therapeutic material, for example of insulin.

BACKGROUND OF THE INVENTION

In a conventional pen injector, such as the Owen Mumford Autopen®, a cartridge containing therapeutic material, for example insulin, is received in a cartridge holder which is connected to a pen body. A needle is typically removably attached to the cartridge holder for delivery of the therapeutic material. The pen body is provided with a mechanism arranged to expel successive single metered doses of therapeutic material from the cartridge via the needle. Such mechanisms generally comprise a plunger which is arranged to engage a piston of the cartridge and to move forward by a predetermined increment in response to a user pressing release button. It will be appreciate that pen injectors are arranged to administer a plurality of repeatable single metered doses and that typically the volume of each individual dose may be variable. Therefore, the mechanism generally further comprises a dose selector, for example a dial, to adjust the movement of the plunger.

It is desirable for pen injectors to be of a compact form so that they can be carried around and used unobtrusively. Further compact injectors may be simple to manufacture, assemble and use with consequent savings in manufacturing and assembly costs, and a lower environmental impact.

SUMMARY OF THE INVENTION

According to a first aspect of the present invention, there is provided a pen injector apparatus for use with a cartridge to deliver a plurality of single metered doses therefrom, the injector apparatus comprising:

a body being arranged to provide a conduit which, in use, provides a fluid communication path between the cartridge and a delivery needle; and a mechanism arranged to expel therapeutic material from the cartridge; wherein the mechanism is arranged to draw therapeutic material from the cartridge into the conduit by negative pressure and discharge a metered dose from the conduit via said delivery needle.

It will be appreciated that the term cartridge as used herein is intended to refer to any suitable container for containing therapeutic material in a pen injector. The cartridge could, for example, include a syringe. In alternate embodiments the cartridge could be integrally formed with or by a portion of the pen injector (for example the injector body or housing).

In a preferred embodiment the mechanism is arranged to discharge the metered dose from the conduit by positive pressure.

Thus, a pen injector assembly according to embodiments of the invention does not require a plunger mechanism to expel therapeutic material from the cartridge (rather the negative pressure provided by the mechanism acts to draw the piston forward as the fluid is discharged). Advantageously, this obviates a limitation to the overall dimensions of known pen injectors which must be of sufficient length to accommodate a mechanism which provides a plunger with a stroke which enables the full volume of the cartridge to be discharged. As such, it will be appreciated that the length of a conventional pen injector is at least double the length of the cartridge.

Additionally, or alternatively, the removal of the plunger in embodiments of the invention may enable a larger capacity cartridge to be used in a conventionally sized pen injector.

The body may comprise a non-return valve arranged to prevent fluid flow from the conduit to the cartridge. The body may comprise a non-return valve arranged to prevent fluid flow from the needle to the conduit. The, or each, non-return valve may be biased to a closed position. As such a minimum pressure difference may be required to overcome the valve and enable fluid flow to or from the conduit.

The front of the body may be adapted to receive a disposable delivery needle (for example a single use sterile needle). For example the body may be provided with interconnecting features for receiving a snap-fit or screw-fit disposable needle assembly. The body may be provided with a septum (typically a rubber membrane) at the front end of the conduit and the delivery needle may be a double-ended needle wherein the rear facing needle tip is arranged to penetrate the septum in use.

The body may be provided with a cartridge needle at its rear end, arranged to penetrate the septum of a cartridge upon assembly of the pen injector assembly. The diameter of the cartridge needle may be greater than that of the delivery needle. A relatively large diameter cartridge needle provides a reduced restriction to fluid being drawn from the cartridge to the chamber and provides an advantageous flow arrangement.

The body may comprise a housing for receiving the cartridge.

The mechanism may comprise a positive displacement pump. A positive displacement pump is a pump which displaces a known quantity of fluid with each action of its pumping element.

In some embodiments the positive displacement pump may be a rotary pump. For example the conduit may comprise a flexible tube and the mechanism comprises a peristaltic pump.

In other embodiments the mechanism comprises a reciprocating pump. For example, the mechanism may comprise a piston pump or a diaphragm pump. In some embodiments the mechanism may be electromechanical, for example a piezoelectric pump. Alternatively, the mechanism may be mechanically actuated by the user (and may, for example, be spring loaded).

The mechanism may further comprise a displacement chamber in fluid communication with the conduit. The displacement chamber may comprise a cylinder and the mechanism further comprises a release button arranged to move a piston or membrane within said cylinder. The release button may for example be mechanically linked to (for example, rigidly connected to) the piston or membrane.

Alternatively, the mechanism may be formed integrally within the body. For example, the mechanism may comprise a first portion of the conduit which is displaceable into a second portion of the conduit so as to reduce the volume of the conduit. For example, the first portion may be slidably mounted within the second portion (i.e. the portions of the conduit may be arranged in a telescopic manner). The portions of the conduit may be biased towards their expanded position.

The mechanism may further comprise a biasing means arranged to return the piston or membrane to its primed position. It will be appreciated that the primed position is typically the position in which the piston or membrane is uncompressed and, as such, in the primed position a metered dose of therapeutic material will have been drawn from the cartridge into the conduit.

The chamber may be arranged at the periphery of the housing. The chamber may be generally elongate and may be substantially aligned with the longitudinal axis of the pen injector. For example, the chamber may be generally annular and may substantially surround the housing. An elongate chamber generally results in a relatively small surface area displacement and a relatively large displacement movement. This may be advantageous in providing mechanical advantage for actuation and may also allow a greater dosing accuracy since small increments in movement of the piston or membrane correspond to only small displacement volumes.

The mechanism may further comprise a dose adjuster arranged to enable a user to set the volume of the metered dose. The dose adjuster may be arranged to adjust the displacement of the pump, for example the dose adjuster may set the stroke of the pump.

Alternatively, the dose adjuster may adjust the number of actuations of the pump in response to a user pressing release button. For example, the dose adjuster may set the number of rotations of a rotational pump such as a peristaltic pump. Accordingly, it will be appreciated that a single metered dose as referred to herein may comprise a plurality of actuations of the mechanism (and may to some extent, therefore, be made up of a series of consecutive discrete discharges) but is the result of a single actuation of the pen injector by a user.

Whilst the invention has been described above, it extends to any inventive combination of features set out above or in the following description or drawings.

BRIEF DESCRIPTION OF THE DRAWINGS

Specific embodiments of the invention will now be described in detail, by way of example only, and with reference to the accompanying drawings in which.

DETAILED DESCRIPTION OF EMBODIMENTS

Figure 1A:
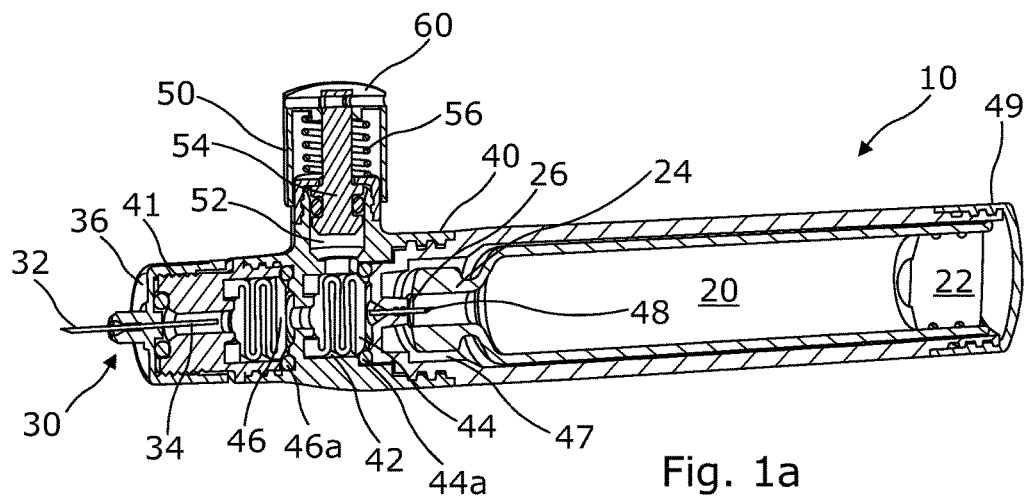
FIG. 1 is a schematic three dimensional cross sectional view of a pen injector according to a first embodiment of the invention.

Front as used herein will be understood to refer to the end of the pen injector assembly (or components thereof) which, in use, are closest to the delivery needle delivery end of the pen injector (i.e. the end which is pointed at the skin). Rear as used herein will be understood to refer to the end of the pen injector assembly (or components thereof) which, in use, are furthest from the delivery needle delivery end of the pen injector (i.e. the end which is pointed away from the skin). Forward and rearward will, likewise, be understood to refer to the directions orientated towards the front and rear of the pen injector assembly.

A schematic cross section of a pen injector 10 in accordance with an embodiment of the invention is shown in FIG. 1. The pen injector 10 is adapted for use with a cartridge or syringe 20 of a therapeutic material such as insulin. The pen injector comprises a housing 40 which receives and supports the cartridge 20 and defines a conduit 42 to provide a fluid communication path between the cartridge 20 and a delivery needle 30. A mechanism 40 is provided to expel a metered dose of therapeutic material from the cartridge 20 in response to the user depressing a release button 60.

The housing 40 comprises a substantially cylindrical elongate body, which may be formed from injection moulded plastic. The housing 40 extends from a front portion, which is provided with an exterior thread 41 to receive a disposable needle assembly 30, to a rear end, which is closed by a removable end cap 49 to allow a cartridge to be inserted or removed. At the front of the cartridge receiving portion of the housing 40 a seat 47 is provided which supports and aligns the head 24 of the cartridge 20 in position such that the cartridge needle 48 may pierce the septum 26 at the front end 24 of the cartridge 20. The conduit 42 in the housing 40 extends from the cartridge needle 48 to the delivery needle 32. A first non-return valve 44 is provided at the rear of the conduit 42 to prevent reverse fluid flow from the conduit 42 in to the cartridge 20. A second non-return valve 46 is provided at the front of the conduit 42 to prevent reverse fluid flow from the needle 32 to the conduit 42. Each non-return valve 44, 46 may be formed from an elastic material such as Acetal (POM) and may be provided with an integral biasing means in the form of a flat compression spring which is of a smaller diameter than the conduit 42 so as not to impede flow. An O-ring 44a, 46a is provided as a seat for each valve 44, 46 to provide good sealing engagement. It will be appreciated however that the valve could be provided with an integral sealing feature such as an upstanding member or ring (an integral sealing member could for example, be provided using a two part construction with an injection moulded plastic biasing means carrying a thermoplastic elastomer sealing member).

The needle assembly 30 comprises a needle holder 36 with an internal thread 37 for engaging the screw thread 41 at the front of the housing 40. The needle is double ended providing a forward facing delivery needle 32 and a rearward facing needle 34 which is arranged to piece a septum (not shown) at the front of the conduit 42.

The mechanism 50 comprises a displacement chamber 52 defined in a sidewall of the housing and in fluid communication with the conduit 42. A piston 54 is provided in the displacement chamber 52 and sealingly engages (via an o-ring around its periphery) the walls of the displacement chamber 52. The rod 55 of the piston 54 extends beyond the chamber 52 and is connected to the release button 60 (which is substantially cup-shaped so as to fit over the exterior of the chamber 52 and enclose the rod 55). A return spring 56, for example a stainless steel coil spring, is provided between the button 60 and the chamber 52 so as to bias the piston towards its primed position as shown in FIG. 1a (as will be explained in further detail below). Stainless steel springs may be preferred for the return spring due to their generally higher resistance to set in comparison to plastic springs.

Operation of the pen injector 10 in accordance with an embodiment of the invention will now be described with particular reference to FIGS. 1a, 1b and 1c. Prior to use a cartridge 20 must be inserted into the rear of the housing 40 by removal of the end cap 49. When fully inserted the head of the cartridge 24 is seated within the seat 47 and the cartridge needle 48 will pierce the septum 26 of the cartridge. A sterile needle assembly 30 is screwed into place on the thread 41 at the front of the pen injector 10 so that the rearward facing needle pierces a septum at the front of the housing. Thus the conduit 42 provides a fluid path between the cartridge 20 and the needle 30. The neutral position of the pen injector mechanism 50 is shown in FIG. 1a, in which the piston 54 is at its upper most position within the displacement chamber 52. In this position both non-return valves 44, 46 are held closed by their integral biasing means.

It will be appreciated that when a new cartridge 20 or needle 30 is inserted into the pen injector 10 it will generally be necessary to prime the pen injector 10 by operating the mechanism 50 (in the manner described below) until any air has been expelled from the conduit 40, needle 30 and/or mechanism 50.

Figure 1B:
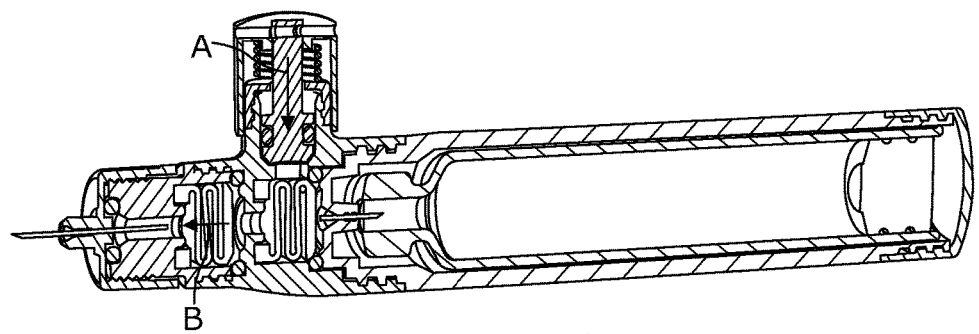
Figure 1C:
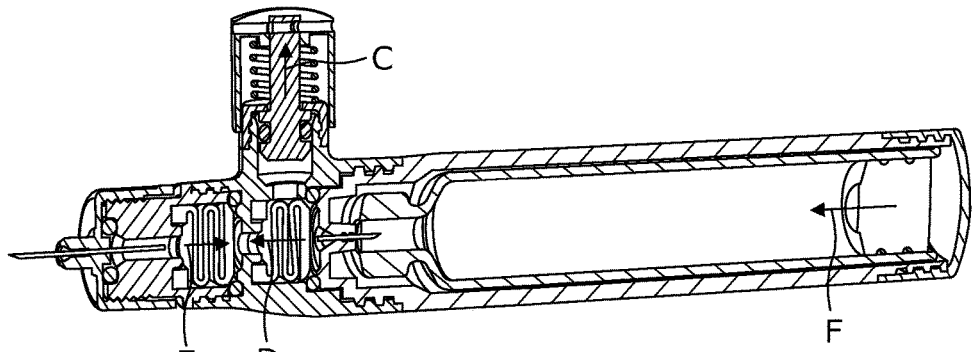

As shown in FIG. 1b, to actuate the pen injector 10, a user depresses the release button 60 towards the body of the pen injector 10 moving the piston 54 in the direction of arrow A. The piston displaces fluid from the chamber 52 into the conduit 42. The resultant positive pressure in the conduit 42 causes the valve 46 to move away from its seat, in the direction of arrow B, thereby enabling a metered dose (of a volume corresponding to the volume of the displacement chamber) to be expelled via the needle 30. It will also be noted that the increase in pressure in the conduit acts upon the front surface of non-return valve 44 and thereby helps to ensure that a good seal (against the O-ring 44a) is maintained to prevent flow back into the cartridge 20. Once a dose has been delivered the pressure in the conduit 42 will reduce and non-return valve 46 will be returned to its closed position (moving backwards, in the direction of arrow E in FIG. 1c) as a result of the integral biasing means and will seal against O-ring 46a.

When a user lifts their finger from the release button 60 the return spring 56 acts to move the release button 60 away from the pen injector 10, in the direction of arrow C. As a result the piston 54 moves out of the displacement chamber 52. Thus, the piston 54 creates a negative pressure in the conduit 42 which acts to causes the valve 44 to move away from its seat, in the direction of arrow D, thereby enabling a metered dose (of a volume corresponding to the volume of the displacement chamber) to be drawn from the cartridge 20 into the conduit 42. It will be also be noted that the decrease in pressure in the conduit acts upon the rear surface of non-return valve 46 (urging it in the direction of arrow E) and thereby helps to ensure that a good seal against the O-ring 46a. As fluid is drawn from the cartridge 20 the cartridge piston 22 is drawn forwards in the direction of arrow F. Once a metered dose has been drawn into the conduit 42 (and the displacement chamber 52 which is in fluid communication therewith) the negative pressure will decrease such that non-return valve 44 will be returned to its closed position (moving backwards in the opposite direction to arrow D) as a result of the integral biasing means and will seal against O-ring 46a.

Figure 2:
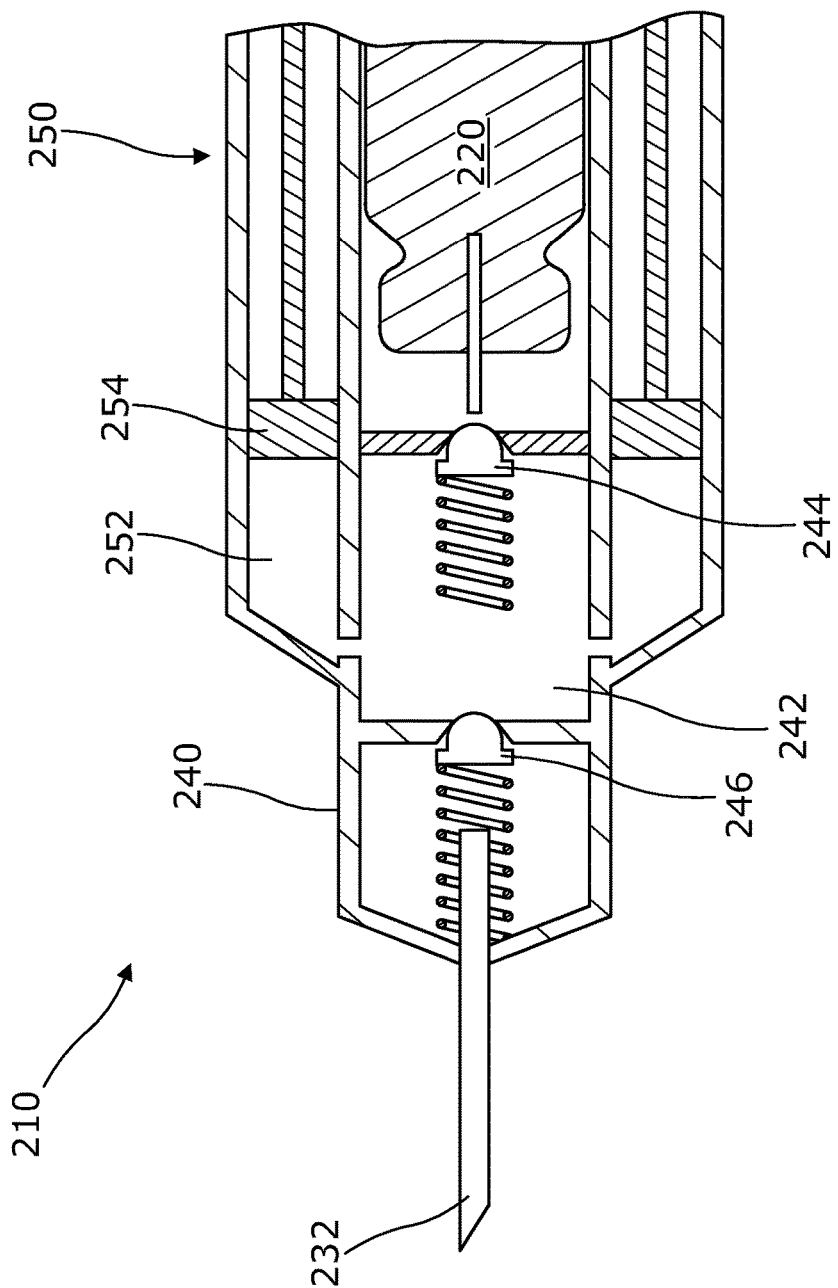
FIG. 2 is a schematic cross sectional view of a pen injector according to a second embodiment of the invention.

A pen injector 210 according to another embodiment of the invention is shown in FIG. 2. This embodiment utilises the same principles as the embodiment of FIG. 1 but is provided with a mechanism 250 which is generally aligned with the longitudinal axis of the pen injector 210. The mechanism comprises a displacement chamber 252 which has an annular profile and is arranged around the periphery of the housing 240. At least one fluid communication port is provided between the chamber and the conduit 242. The piston 254 has a complimentary annular profile to the displacement chamber 252 and is movable parallel to the longitudinal axis of the pen injector 10 (rather than transverse as in the embodiment of FIG. 1).

It may be noted that the non-return valves 246, 244 of the embodiment of FIG. 2 are of a different profile to those of the embodiment of FIG. 1. In this embodiment each valve 244, 246 comprises a substantially domed sealing member which is arranged to seal against a tapered seal seat. Such an arrangement provides a sealing engagement which is less sensitive to any tilt of the valve (and may effectively be self-centring).

Where there is a need to deliver a variable dose of therapeutic agent the action of the piston 54, 254 in either of the preceding embodiments may be altered to vary the displacement from a single actuation cycle of the mechanism 50, 250. For example, a dose selector could be provided which adjusts the stroke of the piston 54, 254. In its simplest form the dose selector could be provided by a threaded engagement between the release button 60 and piston 54 such that the return position of the piston 54 can be set by rotation of the release button. Alternatively a dose selector may be provided which sets the position of a mechanical stop to limit the extent to which the piston 54, 254 can move into the displacement chamber 52, 252.

Figure 3:
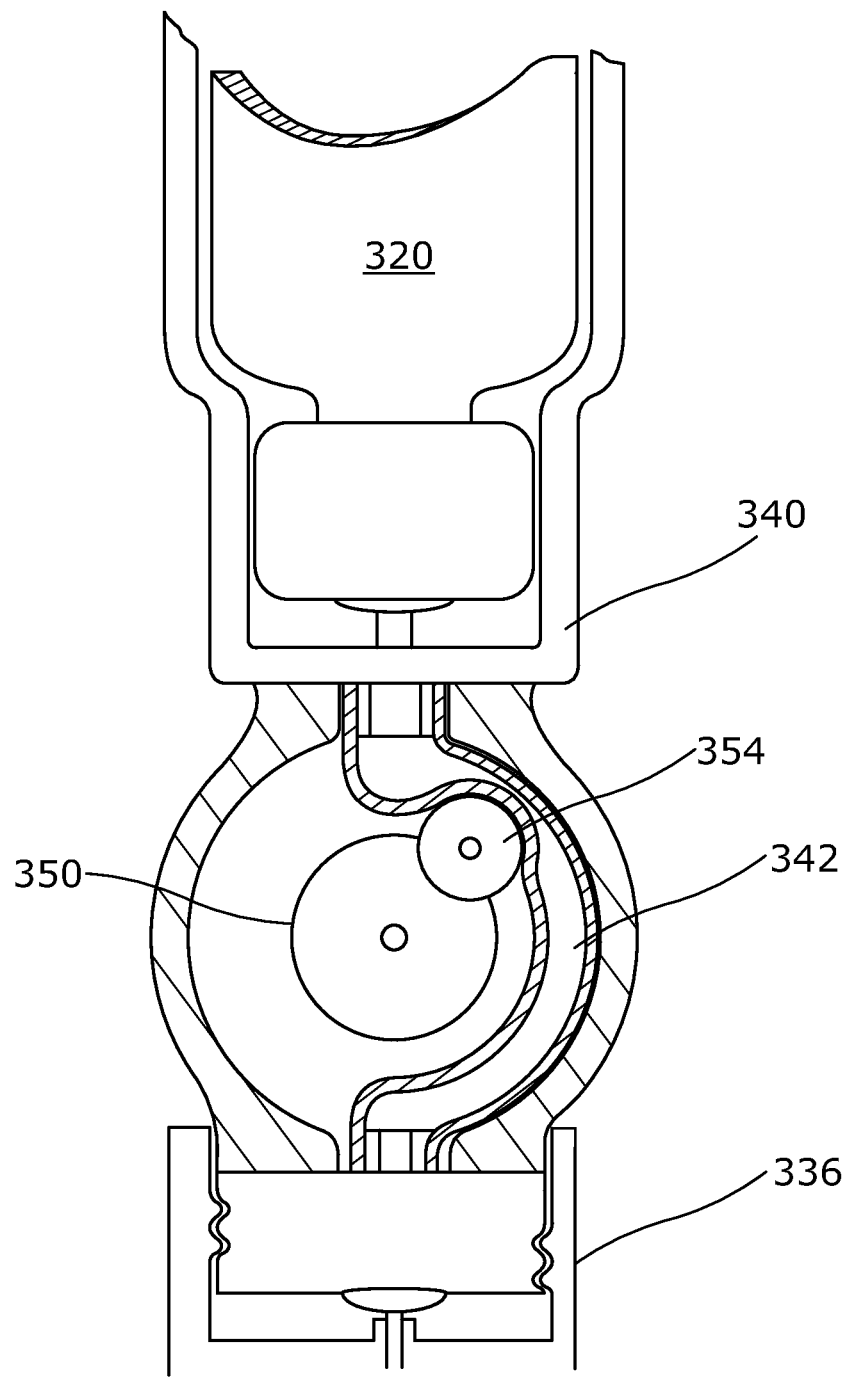
FIG. 3 is a schematic cross sectional view of a pen injector according to a third embodiment of the invention.

A further pen injector 310 according to an embodiment of the invention is shown in FIG. 3. In this embodiment the conduit 342 comprises a flexible tube and the mechanism 350 comprises a peristaltic pump. The peristaltic pump 350 comprises a displacement member 354 which is arranged to pass over the conduit 342 and compress a section of the flexible tube. The displacement member is typically a roller connected to a rotary actuator 355 which rotates across the tube which is held within a generally circular pump casing defined within the housing 340 of the injector pen 310. As the roller 354 turns, the part of tube 342 under compression is pinched closed thus forcing the fluid ahead of the compression point to be pushed through the conduit and expelled from the needle 330. Additionally, as the tube 342 opens to its natural state after the passing of the roller 354 a negative pressure is induced within the tubing which acts to draw fluid from the cartridge 320 into the conduit. The volume of a metered dose may be defined by the number of rotations of the roller 354 and the sizing of the tube 342.

Although the invention has been described above with reference to one or more preferred embodiments, it will be appreciated that various changes or modifications may be made without departing from the scope of the invention as defined in the appended claims.

For example, the skilled person will appreciate that while the embodiment above relates to a durable (or refillable) pen injector in which the cartridge (or syringe) of therapeutic material is arranged to be replaceable (and as such the cartridge is not an essential feature of the invention) other pen injectors may be single use (or pre-filled). For example a single use pen may be provided with a cartridge (or syringe) within the pen and is non-removable such that the pen is disposed of after all of the therapeutic material has been expelled therefrom.

Further, the skilled person will appreciate that the particular arrangement in which the pen injector apparatus of the above embodiment engages the cartridge is not essential and that other arrangements may be within the scope of the invention. By way of example, the apparatus according to an embodiment of the invention could be provided in the form of a multiple or single use attachment which is attached to a cartridge (or syringe) or a housing containing the cartridge (or syringe). The apparatus could, for example, be provided integrally with a needle assembly (for example the body of the apparatus in which the conduit is provided could be the body of the needle assembly).

The invention claimed is:

1. A pen injector apparatus for use with a cartridge to deliver a plurality of single metered doses therefrom, the injector apparatus comprising:

a body configured to receive and support a cartridge of therapeutic material, the body being configured to receive a delivery needle at a forward end, the body defining:
  a seat for receiving a head of the cartridge, wherein the seat comprises a cartridge needle arranged to penetrate a septum of the cartridge when the cartridge is seated within the seat, and
  a conduit which, in use, provides a fluid communication path between the cartridge, the cartridge needle and the delivery needle; and
a mechanism in fluid communication with the conduit, the mechanism arranged to apply a negative pressure at an interface with the cartridge needle to draw therapeutic material out from the cartridge into the conduit, and to discharge a metered dose of the drawn therapeutic material present in the conduit out through said delivery needle.

2. The pen injector apparatus as claimed in claim 1, wherein the body comprises
  a first non-return valve arranged to prevent fluid flow from the conduit to the cartridge; and
  a second non-return valve arranged to prevent fluid flow from the delivery needle to the conduit.

3. The pen injector apparatus as claimed in claim 1, wherein the body is adapted to receive a disposable delivery needle.

4. The pen injector apparatus as claimed in claim 1, wherein a diameter of the cartridge needle is greater than that of the delivery needle.

5. The pen injector apparatus as claimed in claim 1, wherein the body further comprises a substantially cylindrical and elongate housing for receiving the cartridge.

6. The pen injector apparatus as claimed in claim 1, wherein the mechanism comprises a positive displacement pump.

7. The pen injector apparatus as claimed in claim 6, wherein the mechanism comprises a reciprocating pump.

8. The pen injector apparatus as claimed in claim 7, wherein the mechanism further comprises a displacement chamber in fluid communication with the conduit.

9. The pen injector apparatus as claimed in claim 8, wherein the displacement chamber comprises a cylinder and the mechanism further comprises a release button arranged to move a piston or membrane within said cylinder.

10. The pen injector apparatus as claimed in claim 9, wherein the mechanism further comprises a biasing means arranged to return the piston or membrane to its primed position.

11. The pen injector apparatus as claimed in claim 8, wherein the chamber is arranged at the periphery of the housing.

12. The pen injector apparatus as claimed in claim 6, wherein the mechanism further comprises a dose adjuster arranged to enable a user to set the volume of the metered dose and wherein the dose adjuster is arranged to adjust the displacement of the pump.

13. The pen injector apparatus as claimed in claim 7, wherein the mechanism further comprises a dose adjuster arranged to enable a user to set the volume of the metered dose and wherein the dose adjuster is arranged to adjust the stroke of the pump.

14. The pen injector apparatus as claimed in claim 1, wherein the mechanism further comprises a dose adjuster arranged to adjust the number of actuations of the mechanism in response to a user pressing a release button.

\* \* \* \* \*